(12) United States Patent
Calderon

(10) Patent No.: US 7,947,030 B2
(45) Date of Patent: May 24, 2011

(54) RETROGRADE PERFUSION OF TUMOR SITES

(76) Inventor: Reynaldo Calderon, Houston, TX (US)

( * ) Notice: Subject to any disclaimer, the term of this patent is extended or adjusted under 35 U.S.C. 154(b) by 108 days.

(21) Appl. No.: 11/026,103

(22) Filed: Dec. 30, 2004

(65) Prior Publication Data

US 2006/0149219 A1    Jul. 6, 2006

(51) Int. Cl.
*A61M 31/00* (2006.01)
(52) U.S. Cl. .................................................. 604/509
(58) Field of Classification Search .............. 604/500, 604/509; 600/10
See application file for complete search history.

(56) References Cited

U.S. PATENT DOCUMENTS

| | | | | |
|---|---|---|---|---|
| 4,714,460 A | * | 12/1987 | Calderon | 604/28 |
| 4,867,742 A | * | 9/1989 | Calderon | 604/28 |
| 4,883,459 A | * | 11/1989 | Calderon | 604/28 |
| 5,011,469 A | * | 4/1991 | Buckberg et al. | 604/6.11 |
| 5,040,540 A | * | 8/1991 | Sackner | 600/485 |
| 5,368,555 A | * | 11/1994 | Sussman et al. | 604/6.05 |
| 5,533,957 A | * | 7/1996 | Aldea | 600/16 |
| 5,597,377 A | * | 1/1997 | Aldea | 600/16 |
| 5,851,985 A | * | 12/1998 | Tepic et al. | 514/2 |
| 6,485,489 B2 | * | 11/2002 | Teirstein et al. | 606/41 |
| 2001/0041862 A1 | * | 11/2001 | Glickman | 604/101.01 |
| 2001/0044598 A1 | * | 11/2001 | Parodi | 604/104 |
| 2002/0115994 A1 | * | 8/2002 | Teirstein et al. | 606/41 |
| 2003/0157024 A1 | * | 8/2003 | Tachibana et al. | 424/9.52 |
| 2003/0225336 A1 | * | 12/2003 | Callister et al. | 600/505 |

OTHER PUBLICATIONS

Goldberger, Ary L., Nonlinear Dynamics, Fractals and Chaos Theory: Implications for Neuroautonomic Heart Rate Control in Health Disease, pp. 6-8.

* cited by examiner

*Primary Examiner* — Kevin C Sirmons
*Assistant Examiner* — Michael J Anderson
(74) *Attorney, Agent, or Firm* — Adams and Reese LLP; Raymond R. Ferrera

(57) ABSTRACT

A system and method permit monitoring and location of a route in vivo and a visible image of that route for retrograde perfusion of a tumor with a therapeutic agent. Once the route is located, the path for flow of therapeutic agent to the tumor is confirmed as being a closed loop. The therapeutic agent is then introduced into the closed loop through retrograde perfusion to treat the tumor. The number of types and amounts of treating agents may be adjusted and observed as the treatment is in progress.

13 Claims, 9 Drawing Sheets
(1 of 9 Drawing Sheet(s) Filed in Color)

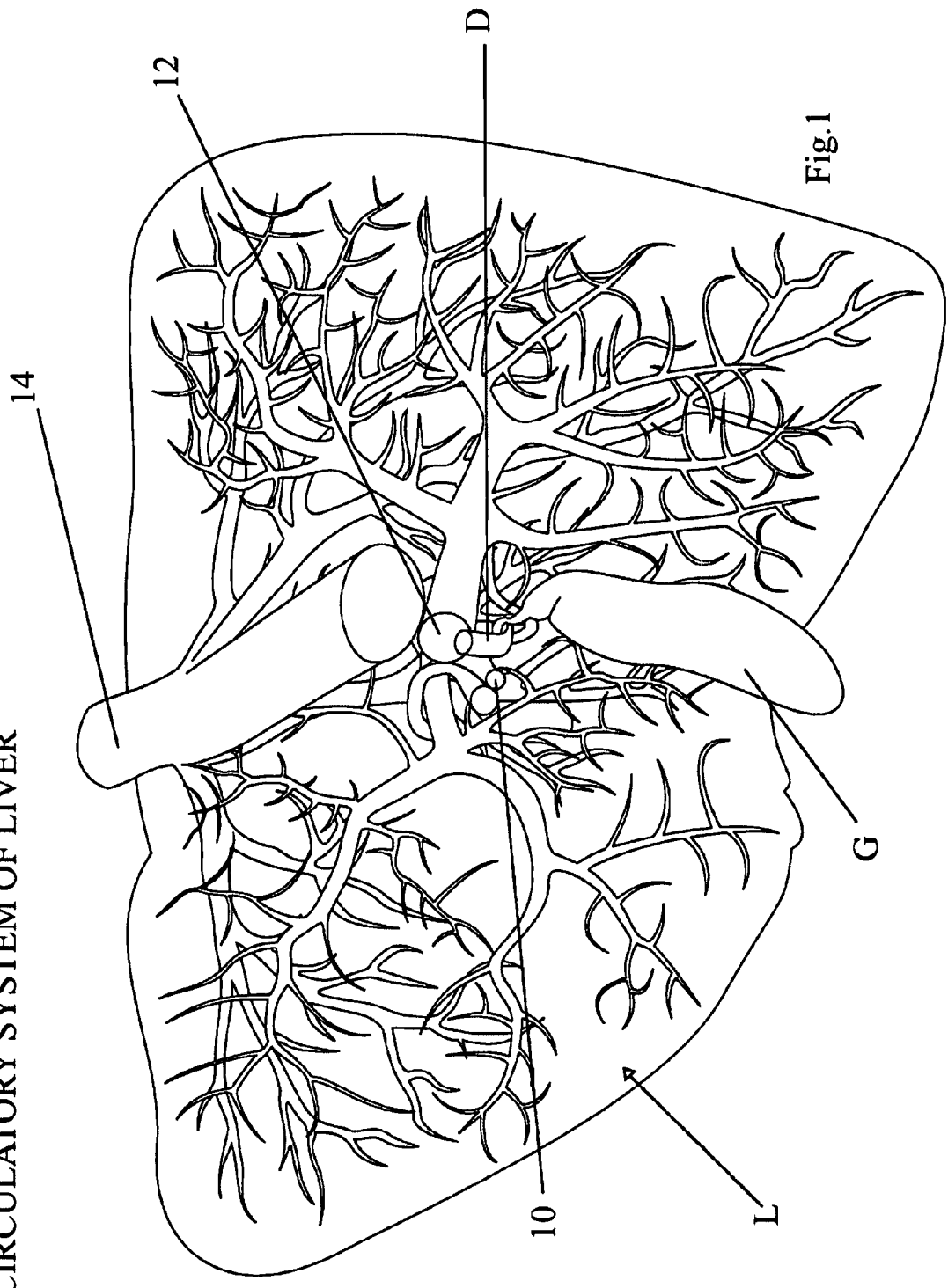

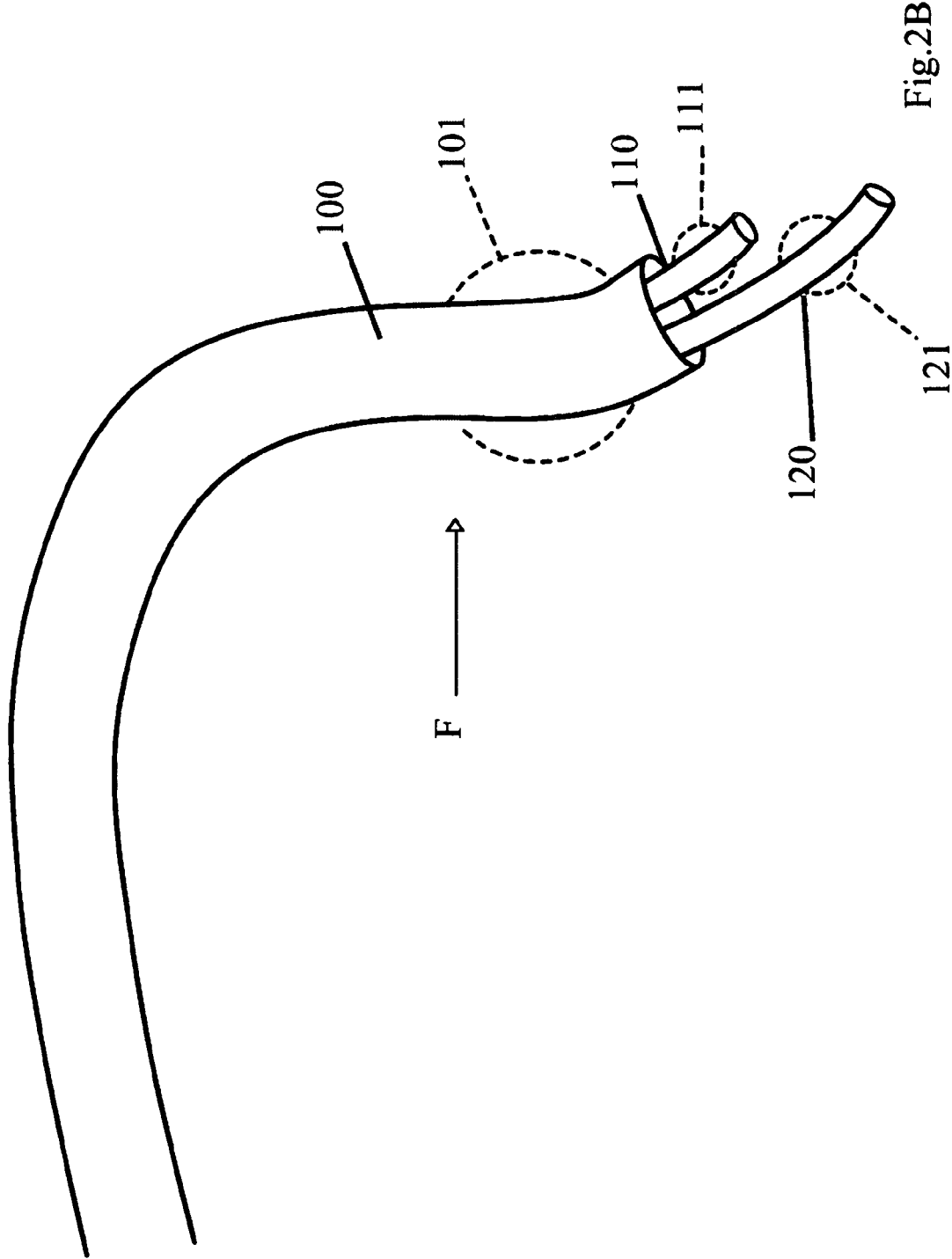

RETROGRADE PERFUSION OF TUMOR SITES

BACKGROUND OF THE INVENTION

1. Field of the Invention

The present invention relates to methods and systems for delivery of therapy to organ sites and to tumor sites in particular. More specifically, the present invention provides a new and improved systems and methods for delivering chemotherapy, gene therapy or other therapeutic agents to diseased or cancerous sites, and particularly to solid tumors.

2. Description of the Related Art

U.S. Pat. Nos. 4,714,460, 4,867,742 and 4,883,459, of each of which Applicant is inventor, relate to methods and systems for study and treatment in situ of tumors in a subject patient's body of retrograde perfusion. Although the techniques of retrograde perfusion have been considered as possibly advantageous and helpful, there has been hesitancy to attempt widespread experimentation using the techniques of these patents. There are also several problems still remaining which have hampered attempts in this area for treatment of tumors, regardless of the method or system proposed.

There has been an uncertainty or blind spot in the delivery procedure with respect to the path of travel or trajectory that a therapeutic agent travels during the infusion or treatment procedure. This has in turn caused a resultant unpredictability regarding the route(s) taken by a therapeutic agent once the agent has been administered by conventional intravenous delivery techniques.

Another problem has involved inadequate uptakes and nonoptimal distribution in tumors in vivo. As has been pointed out in Applicant's earlier U.S. patents: The tumor blood flow is thus impaired, measuring only two to fifteen percent of that of the surrounding tissue, and this impaired circulation distinguishes the cancer vasculature. The probability of blood flow through the V—V shunts is far less than the probability of blood flow through the normal vasculature. Therefore, in any attempt to deliver chemotherapy to a tumor, the likelihood that the drug will spread to the remainder of the body is far greater than the likelihood that it will reach the tumor. There were problems in making certain that the tumor (rather than the entire body) received a significantly high dose and duration of exposure to the treatment agent. Another problem was in determining and controlling the routes of drug delivery within a target site, as well as that of withdrawing any excess drug.

A final problem is isolation of the treatment agent to the area of the tumor in the patient. There are certain agents which have proven effective in chemotherapeutic treatment of tumors, but which have potentially severe side effects. An example is doxorubicin, available under the trademark ADRIAMYCIN®, which has been used as an anti-cancer drug for a number of years. That composition has been used to treat many forms of cancer including cancer of the breast and stomach, lymphoma and multiple myeloma. However, severe side effects have ensued. A common side effect if dosage is not controlled has been dilated cardiomyopathy. The use of this chemical to treat tumors has been limited, when systemically administered, due to its toxic side effect on the patient's heart.

SUMMARY OF THE INVENTION

Briefly, the present invention provides a new and improved method of retrograde venous perfusion of a tumor in a patient's body and a treatment unit for such perfusion.

According to the method of the present invention, an infusion catheter is positioned within vasculature of a target vessel in the patient's body near the tumor. A withdrawal catheter is positioned within the vasculature of the target vessel distally of the infusion catheter and near the tumor. A venous pressure catheter is positioned within the vasculature of the target vessel intermediate the infusion catheter and the withdrawal catheter. In this manner, a closed loop flow path is formed between the positioned infusion catheter and the positioned withdrawal catheter through the target vessel. Venous pressure is monitored in the closed loop flow paths, and fluids are then circulated through the closed loop flow path.

The fluids circulated at different times may be different for different purposes. The first fluid is a saline fluid to determine that a closed loop flow path is achieved. The next fluid to be circulated is a dye-containing solution, so that a visible image of the closed loop flow path is available. Finally, a treatment fluid or treatment fluids may then be subsequently circulated.

The treatment unit according to the present invention takes the form of a withdrawal catheter for positioning within venous vasculature of a target vessel in the patient's body near the tumor, along with an infusion catheter located within the withdrawal catheter for positioning within the venous vasculature of the target vessel vasculature of the infusion catheter. The treatment also includes a venous pressure monitoring catheter for positioning within the vasculature of the target vessel intermediate the infusion catheter and the withdrawal catheter. A pressure transducer may be mounted either within the venous pressure monitoring catheter, or externally of the patient's body. By virtue of the position of the three catheters relative to one another and to the target vessel, a pressure differential is established in the catheter network between the tip of the infusion or push catheter and the tip of the withdrawal or pull catheter, between the push catheter and the pull catheter, between the withdrawal or central venous pressure catheter and the push catheter, and between the catheter network and the control space of the venous vasculature. The perfusion treatment thus is in accordance with fluid dynamic and flow principles.

There is, however, no need to establish or define specific fluid flow equations of motion explicitly in order to verify that proper perfusion fluid flow paths and relations are established. The control or treatment unit functions as an analog fluid dynamic computing unit that during its use and operation implicitly computes the solution to the equations of motion for the network, and performs the perfusion treatment according to the desired flow paths and relationships. This is done without resorting to the explicit use of calculations, numbers, mathematical equations or physical equations of motion and such; the control unit during its use performs those kinds of computational tasks.

Two examples or models help to explain by analogy the kinds of differential equations of motion that are implicitly solved by operation of the control unit. One is a water-flow model that cascades; the other is a moving crowd model.

In the water-flow model, the size and shape of the catheters influence the motion of fluid through the catheters. Also, the motion of fluid in parallel and opposite directions, and orientation through the catheters and through the vascular beds obeys the physical laws related to pressure, flow rate, and volume. In the moving crowd model, the size and shape of the catheters influence the movement of particles through the catheters. Also, the movement of particles through the network conforms to the physical laws related to pressure, flow rate, and volume.

BRIEF DESCRIPTION OF THE DRAWINGS

The patent application file contains at least one drawing executed in color. Copies of this patent application publication with color drawings will be provided by the Office upon request and payment of the necessary fee.

A better understanding of the present invention can be obtained when the detailed description set forth below is reviewed in conjunction with the accompanying drawings, in which:

FIG. 1 is photograph of a highly simplified model of the circulatory system in the liver of an animal.

FIGS. 2A and 2B are isometric views of catheter system portions of the present invention.

DETAILED DESCRIPTION OF THE PREFERRED EMBODIMENTS

Figure 2A:
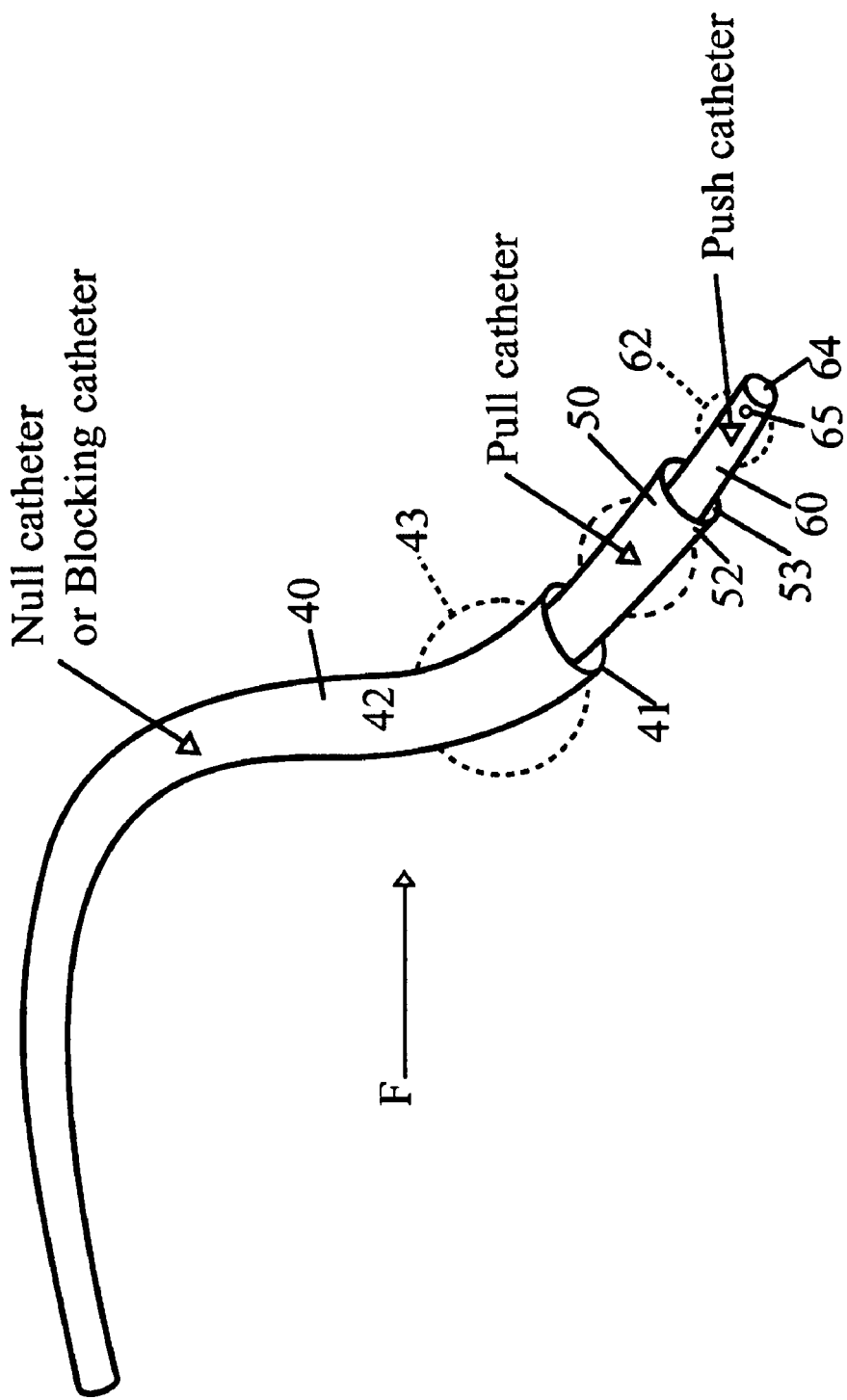

In the drawings, a photographic model of the circulatory system of blood flow the liver of an animal, in this case a human, is shown in FIG. 1. The liver L is located in the body in communication through the common bile duct D with the gallbladder G. As indicated at 10, the hepatic artery connects to and transports blood into the liver L for the purpose of bile production, protein production, blood detoxification and other liver functions.

In the treatment of tumors in other organs, a similar approach applies. In the case of a tumor of the kidney, for example, the renal artery carries blood from the aorta to the kidney while the renal vein carries blood from the kidney to the inferior vena cava. For the purpose of retrograde perfusion, access to a tumor of the kidney would be via the inferior vena cava to the renal vein.

Further, retrograde perfusion can also be performed via percutaneous access to any organ whereby the venous drainage of the target organ is accessed directly via an incision. In any given organ, the point of reference for the process of retrograde perfusion is the site of the venous drainage from the organ.

The other major blood flow paths in the liver in addition to the hepatic artery 10 are also indicated in FIG. 1, including the portal vein as indicated at 12 and the inferior vena cava as indicated at 14. Blood enters the liver L from the heart via the hepatic artery 10 and from the stomach, intestines and other parts of the digestive tract through the portal vein 12.

Figure 5:
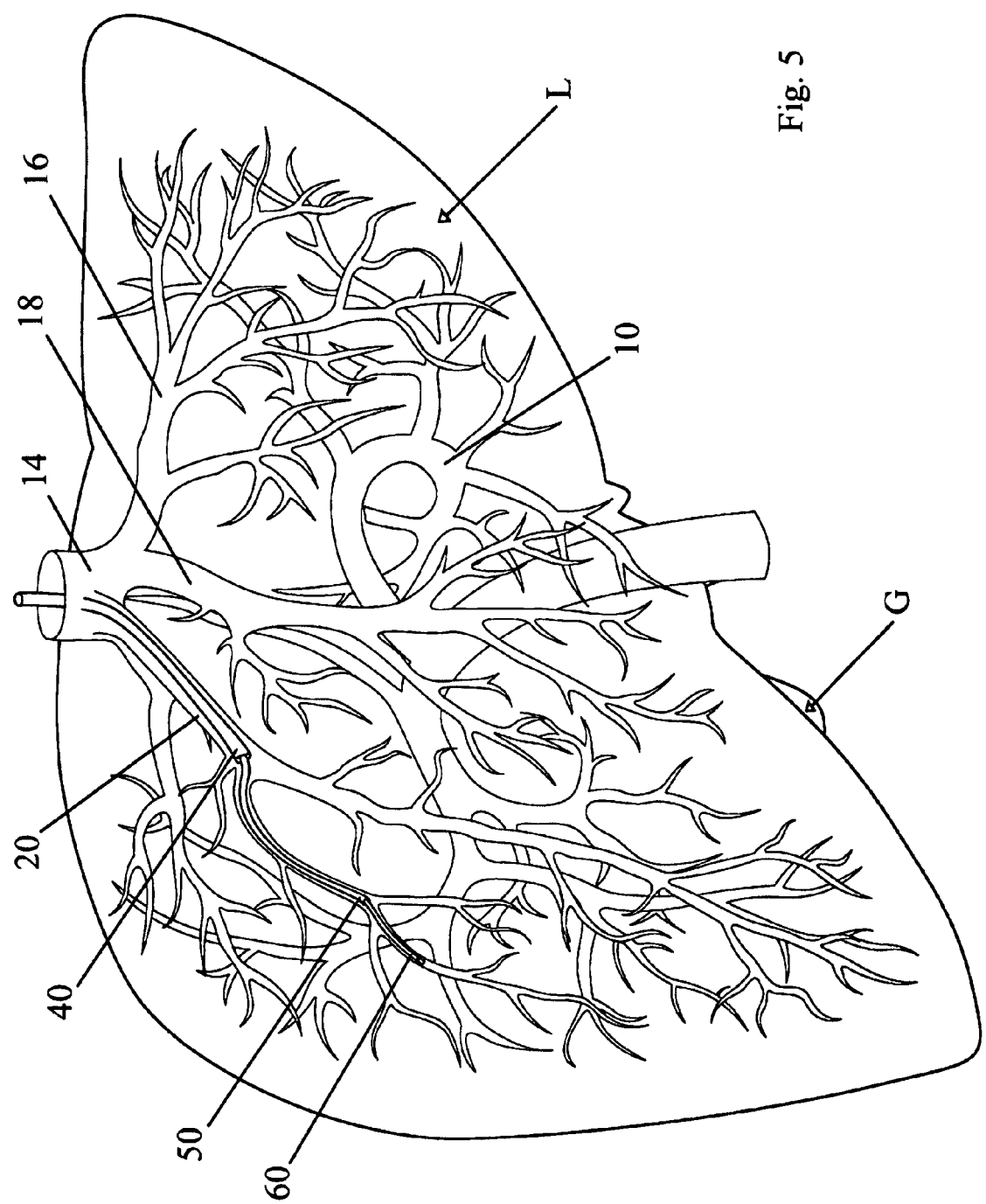
FIG. 5 is a schematic drawing of a liver receiving treatment during a procedure with a perfusion system of the present invention.
Figure 6:
FIG. 6 is a photograph of a model like that of FIG. 1 with a catheter according to FIG. 2A.

Incoming blood from the hepatic artery 10 and portal vein 12 merges and passes through the liver L to a series of hepatic veins (FIG. 5), including the left hepatic vein 16, a middle hepatic vein 18 and a right hepatic vein 20. The hepatic veins 16, 18 and 20 collect blood as it is processed in the liver L and empty into the inferior vena cava 14. As can be seen in FIG. 1, the hepatic artery 10 and the veins 12, 16, 18 and 20 are only the major blood flow paths through the liver L. There are as indicated in FIG. 1 a considerable number of other separate and distinct smaller or minor blood flow paths or veins branching off and in flow communication with the major flow paths. Because of the number of them, no reference indicators are assigned them in FIG. 1.

Such branching structures are examples of fractal architecture found commonly in a wide variety of physiological systems including the respiratory, circulatory, and nervous systems. Examples of fractal anatomy can be seen in anatomical structures such as the hepatic arterial and venous trees shown in FIG. 1.

As opposed to classical geometric forms that are smooth and regular having integer dimensions such as one, two and three for line, surface, and volume, fractals have a fractional dimension between one and two and exhibit a pattern of repeating smaller scale sub-patterns that resemble the larger scale pattern, a property terms self-similarity or scale invariance. Such fractal scaling is seen in the lungs, the bronchial tubes, capillaries, intestinal lining, and bile ducts; and the heart comprises various fractal networks including the coronary arteries and veins, the fibers binding the valves to the heart wall, the cardiac muscles themselves, and the His-Purkinje system that transmits electrical impulses from atrium to ventricle.

Fractal structures exhibit another significant property, the relationship between perimeter and area. A physiologic advantage of self-similar fractal structures is that they serve a common physiological function that has been characterized in the literature as "rapid and efficient transport over a complex, spatially distributed system. In the case of the ventricular electrical conduction system, the quantity transported is the electrical stimulus regulating the timing of the cardiac contraction. For the vasculature, fractal branchings provide a rich, redundant network for distribution of O2 and nutrients and for the collection of CO2 and other metabolic waste products. A variety of other organ systems contain fractal structures that serve functions related to information distribution (nervous system), nutrient absorption (bowel), as well as collection and transport (biliary duct system, renal calyces). "Nonlinear Dynamics, Fractals and Chaos Theory: Implications for Neuroautonomic Heart Rate Control in Health Disease", Ary L. Goldberger, 6-8.

Further, the model liver L of FIG. 1 although seemingly detailed is instead conceptual in that only a certain number of even the minor blood flow paths are represented, due to limits on the ability to form tangible representations of a number of the minor flow paths. The liver as in the case of other body organs or regions has in actuality a number of other smaller blood veins and flow paths, which are hard to discern and visualize. Further, the circulatory system embodied in the model of the liver L is a tangible, physical manifestation of the blood flow paths at a fixed moment.

Similar blood flow structure exists in other body organs as well. Accordingly, the liver as illustrated in FIG. 1 is given by way of example. It should be understood that the perfusion techniques of the present invention to be described below are equally applicable to other organs and portions of the body.

In the human or other animals, the flow of blood in flow paths through an organ such as the liver fluctuates in both pressure and flow rate in response to heart rate and blood pressure. As a result when an organ under investigation is viewed through body imaging systems as a display image by a treating physician, the organ appears much like a cloud or blurred image. Thus, in treating an organ, the display images are less articulated and defined in the body than the idealized, simplified flow path models as illustrated in the photograph of FIG. 1.

As mentioned above, it is known that there are chemotherapeutic agents of demonstrated effectiveness in treatment of tumors. However, their use has been significantly limited by the undesirable side effect of systemic toxicity on other organs or parts of the body. Although earlier retrograde perfusion efforts, as exemplified in Applicant's United States patents mentioned above, have shown promise, certainty of the localization and isolation of the area of the patient's body receiving a chemotherapeutic agent is still a desirable goal. This holds true for chemotherapeutic agents of any type, but particularly those with undesirable systemic side effects, whether toxicity or some other undesirable effect.

Figure 3:
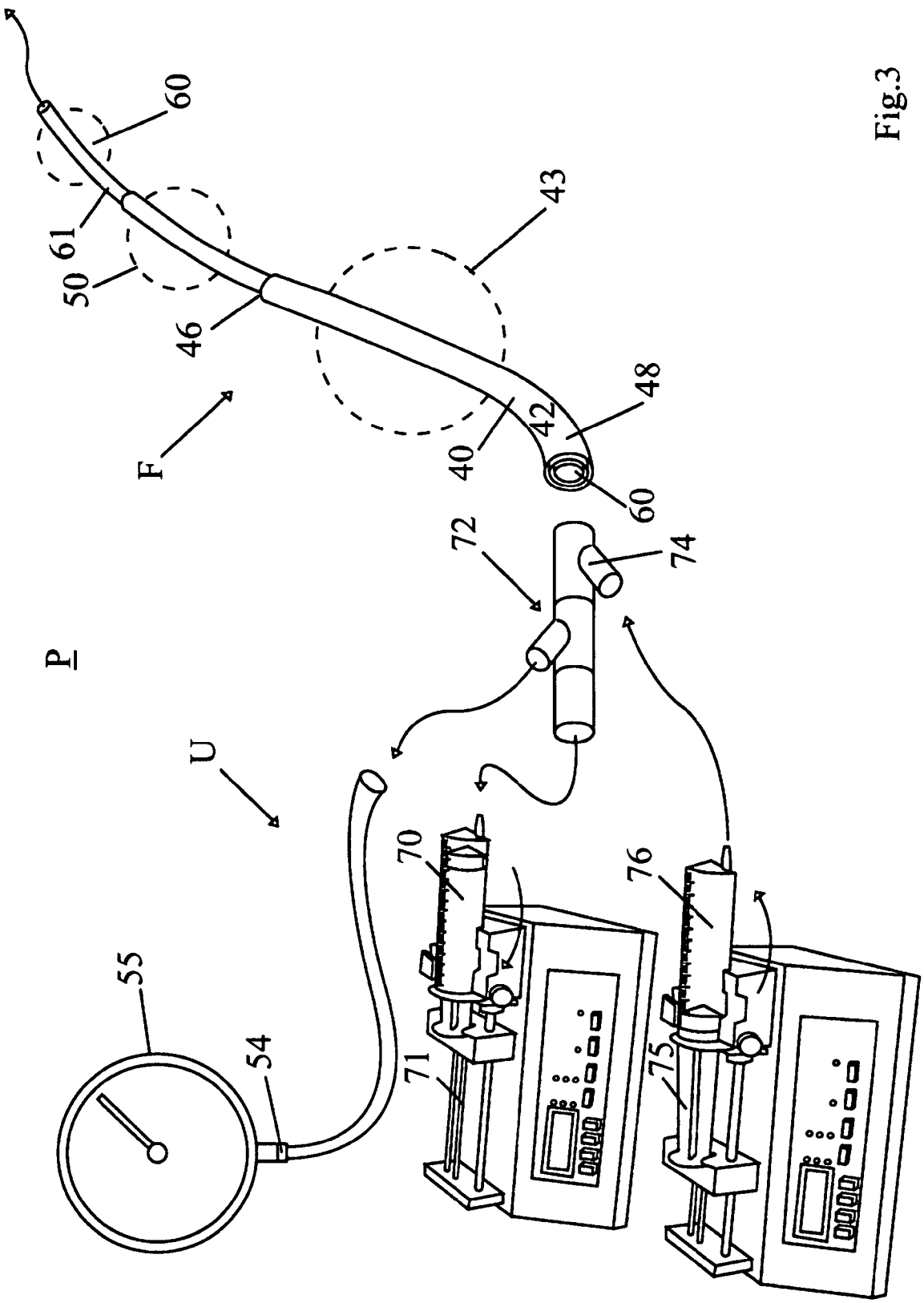
FIG. 3 is a schematic diagram of a perfusion system according to the present invention.
Figure 4:
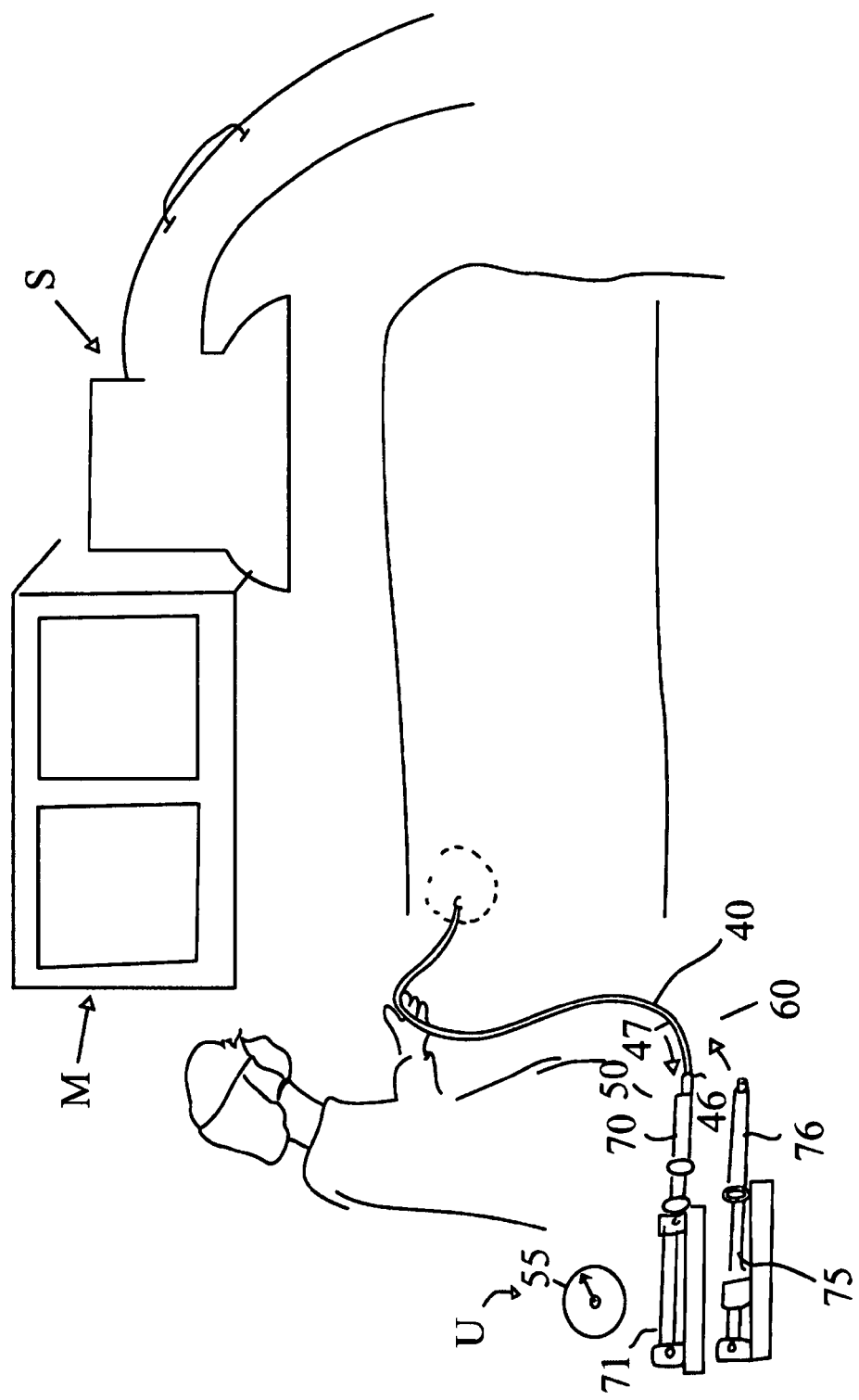
FIG. 4 is a schematic diagram of a treatment procedure with the perfusion system of FIG. 3.

The present invention provides a method and apparatus for retrograde perfusion of a patient with a therapeutic agent in a flow, controlled, pressure regulated in vivo closed loop in the vasculature of the patient. The apparatus of the present invention takes the form of a retrograde perfusion system P that includes a flow control or administration unit F (FIGS. 2A and 2B) that is introduced into the body of the patient. The flow control unit F is in fluid communication with an external unit U (FIGS. 3 and 4) with monitors and pumps with which treating physicians and their staff may administer the therapeutic agent, even one with substantial system toxicity, by retrograde perfusion in a closed loop, pressure regulated flow route in vivo. Typically, one or more visual monitors M are provides to display images formed for example by fluoroscopy or by computerized axial tomography or CAT scanner S. The monitors M allow the treating physician or physicians to gain visible confirmation of the formation, establishment and operation of the in vivo flow route.

The internal flow control unit F is a multicatheter system introduced into the vascular system of the patient at a suitable location, for example by femoral or neck cutdown, depending on the organ or portion of the patient's body to receive the therapeutic agent. The flow control unit F includes three catheters that may be configured to be concentrically mounted with each other (FIG. 2A) or may have two of the catheters separately contained (FIG. 2B) within a third or larger outer catheter.

In a flow control unit 30 according to the present invention, a larger catheter 40 to extract or pull fluid from the in vivo loop formed in the vasculature of the patient has a central venous pressure or cvp catheter 50 and an infusion or push catheter 60 concentrically and telescopingly mounted therein. As will be set forth below, each of catheters 40, 50 and 60 is positioned with a proximal end within a vessel in the patient's vasculature and a distal end in flow communication with the external unit U of the perfusion system P.

The catheters of the flow control unit 30 are located near the tumor to be treated. In the context of the present invention, near the tumor is intended to connote that the tumor is located in vasculature between the infusion catheter 60 and withdrawal catheter 40. Further, near the tumor is intended according to the present invention to signify that the catheters of the flow control unit 30 are located in the vasculature of the patient with no unoccluded intervening vasculature present in the area between the infusion catheter 60 and withdrawal catheter 40.

The larger or pull catheter 40 is a size, such as a 10 to 12 French or Fr. sheath 42, with a compliant distal balloon 43 or other comparable mechanism for occluding the vessel of interest in the patient. The pull catheter 40 also has a large enough internal diameter to accommodate the push catheter 60 and the central venous pressure catheter 50 concentrically and coaxially within it. Alternatively, the pull catheter 40 may, if desired, be sufficiently large, such as 14 Fr. sheath, that its distal end 41 may be used to occlude a vein without balloon 43.

The length of the sheath 42 of pull catheter 40 may vary based on the organ site and the venous access, for example neck or femoral cutdown. A sheath length of approximately 34 cm typically permits the catheter 40 be routed via a jugular cut-down procedure to the target organ site. The sheath 42 preferably is suitably flexible to permit extensive maneuvering and routing in the vasculature. However, the sheath 42 should also be structurally sturdy enough to avoid kinking or collapsing under pressure. The sheath 42 has a guide wire and/or introducer for proper placement. The guide wire or introducer is removed when the pull catheter 40 is established at the proper in vivo, closed loop position. An outflow port 46 (FIG. 4) on the pull catheter 40 is provided for the purpose of withdrawing fluids. A distal end 47 of the pull catheter 40 routes the outflow from pull catheter 40 to a withdrawal syringe 70 (FIG. 3) of the external unit U. A proximal end 48 of the pull catheter 40 is connected via a T-port 72 to the withdrawal or pull syringe 70 for withdrawing fluids.

The push or infusion catheter 60 has similar properties of length, flexibility and structural strength to those of the pull or withdrawal catheter 40. The push catheter 60 in the embodiment of FIG. 2A has a sheath 61 with an outer diameter of from about 3-7 Fr. fitted with a compliant balloon 62 for occluding a vessel. The sheath 61 is also provided with a radio-opaque proximal tip 64 for visualizing the position of the catheter proximal end within a vessel. The push catheter 60 has an outer diameter that enables it to fit coaxially and telescopically within the central venous pressure catheter 50 and the pull catheter 40. An opening 65 at the distal tip 64 of the input catheter 60 serves the purpose of infusing fluids. A proximal end 67 of the input or infusion catheter 60 is connected via a T-port 74 of the external unit U to a push syringe 76 for infusing fluids into the in vivo loop in the patient.

The central venous pressure or cvp catheter 50 has similar properties of length, flexibility and structural strength to those of each of the push catheter 60 and the pull catheter 40. In the embodiment shown in FIG. 2A, the central venous pressure catheter 50 has a sheath 51 with an outer diameter intermediate that of the push catheter 60 and the pull catheter 40. The central venous pressure catheter 50 is fitted at a distal end 52 with a port or opening 53 and in fluid communication with a pressure transducer 54. The pressure transducer 54 may, if desired, be located with the external unit U in fluid communication through the port 53 with pressure and flow rate conditions in the closed loop formed in the patient's vasculature by the present invention between the infusion catheter 60 and the pull catheter 40. The pressure transducer 54 allows monitoring of central venous pressure in the closed loop to be certain that a stable central venous pressure is present between the push catheter 60 and the pull catheter 40. A gauge or meter 55 or other form of pressure readout indication or display, as indicated schematically at 55, is present in the external unit U to indicate the central venous pressure sensed by transducer 54 to the monitoring/treating physician(s).

The pressure transducer 54 and indicator gauge or readout device 55 are connected to the central venous pressure catheter 50 for monitoring and tracking the central venous pressure in the patient's vasculature in the organ to receive perfusion between the push catheter 60 and pull catheter 40. The pressure transducer 54 and indicator gauge 55 thus provide the physician(s) with information about fluid conditions so that after formation of the closed loop at the treatment site, a steady state or frame of fluid pressure reference is obtained there. During the subsequent perfusion/treatment cycle, fluctuations or transient changes sensed through the transducer 54 and central venous pressure catheter 50 provide the physician with valuable information to closely control and monitor the infusion and extraction of fluid at the treatment site.

By virtue of the position of the three catheters relative to one another and to the target vessel, a pressure differential is established in the catheter network. One such pressure differential relationship is that of a transient stability established between the tip of the push catheter and the central venous pressure catheter. Another is the pressure differential between the push catheter and the background noise of the venous liver circulation. The pressure differential thus established is in a forward orientation and direction from the tip of the infusion catheter to the venous circulation.

In the opposite orientation and direction, a pressure differential is established between the pull catheter and the central venous pressure catheter. Another pressure differential is established between the venous circulation and the pull catheter. The perfusion treatment according to the present invention thus is in accordance with fluid dynamic and flow principles.

The push syringe 76 of the external unit U as connected via the T-port 74 to the push catheter 60 measures and injects the desired amount of various fluids during the treatment cycle, whether saline, dye, or therapeutic drug to be infused.

The external unit U also includes the withdrawal syringe 70 that is connected via the T-port 72 to the pull catheter 40 for collecting the spent fluid used during treatment, whether saline, dye, or drug, once the fluid has been infused and passed through the closed loop treatment site. Each of the syringes 70 and 76 is further connected to its respective associated pump 71 and 75, such as a Harvard type infusion pump, for the purpose of infusing and withdrawing the saline, dye, or drug, as the case may be. The infusion by syringe 76 and withdrawal by syringe 70 is done by the physician with the external unit U at the desired flow rate, and also to set up the differential pressure and related motions to physically impart characteristics to the fluids at the perfusion treatment site.

The operation of the syringes 70 and 76 and their respective associated pumps may also be automated via a computer and appropriate software program. In such a case, the computer and software operate according to established settings, taking into account various factors, such as:

(1) the volume of fluid (saline, dye, drug) to be infused;
(2) the rate of infusion of the fluid(s);
(3) the time duration of the infusion; and
(4) the ratio of withdrawal rate to infusion rate.

In addition, an appropriate computer system and software can permit a database to be formed and maintained. Such a database would allow data to be retained in order to correlate the location of various perfusion treatment sites, and established settings, as well as the factors mentioned above, along with the type and nature of images or fractals obtained therewith. Such a database would allow a physician greater flexibility in treatment by retrograde perfusion.

In the operation of the present invention, the initial phase is that of assembly of the flow control unit F based on the planned perfusion treatment, the treatment site and other factors. Assembly can be regarded as a sequential assembly phase. The catheters 40, 50 and 60 are combined externally in sequence and placed sequentially coaxially relative to one another. In one possible configuration of the catheters shown in FIG. 2A, the pull or proximal catheter 40 is the outermost catheter of the three. Coaxially positioned within the pull catheter 40 are the catheters 50 and 60, which are sequentially placed based on their respective sizes. In the embodiment of FIG. 2A, the next catheter to be positioned coaxially within the pull catheter 40 is the central venous pressure or cvp catheter 50. Coaxially positioned within the central venous pressure catheter 50 is the innermost chamber and catheter, the push or distal catheter 60.

Assembled telescopically one inside the other in this manner, the three catheters 40, 50 and 60 form the internal flow control unit F. As noted above, it may in certain instances be desirable for the catheters 40, 50 and 60 to have an alternate configuration. For example, as shown in FIG. 2B, an outer catheter 100 with balloon 101 serves as the pull catheter, and catheters 110 and 120 with their respective balloons 111 and 121 are separately and not co-axially mounted with each other serve as the central venous pressure catheter and the infusion or push catheter, respectively. Appropriate connections to the respective syringes and pumps of the external unit U are made for these purposes.

Alternatively, the outer catheter 100 shown in FIG. 2B may serve as the central venous pressure catheter and the catheter 110 serve as the pull catheter, if desired. Again, appropriate connections to the external unit U are made for this purpose.

The control unit F with catheters of the various configurations identified above allows the physician to develop various strategies for how to organize differential pressures externally between the push syringe 76 and the pull syringe 70 for moving fluid outward through the perfusion system P to the closed loop to the treatment site and returning. The fluid movement is accomplished using the pressure-monitoring central venous pressure catheter 50 to coordinate, monitor, and visualize transient changes in central venous pressure sensed through catheter 50 during the operation of the internal control unit F.

The assembly of the control unit F and the final determination of its configuration is adjustable with regard to the relative longitudinal placement of the catheters 40, 50 and 60 with respect to each other. Further, the configuration and location of the catheters 40, 50 and 60; the infusion flow rate and pressure; and the extraction flow rate and pressure may be monitored and adjusted "on the fly" while the retrograde perfusion is under way. The adjustments may be based on the variable requirements of the target vessel (i.e. vessel diameter, length) as well as on the objectives of the planned, controlled treatment that is to be performed to frame a search for a missing piece while trying to frame a strategic action and a strategic course of retrograde perfusion treatment, including apriori goals of a visual representation of mapping of a volumetric shape based upon an emergent shape.

A visual representation (FIG. 8) of the type shown on video monitor M illustrates the successful placement of the catheters 40, 50 and 60 in order within a target vessel, in this case an animal liver L. The pull catheter 40 is inserted first in sequence into the external jugular vein and routed with the help of guide wire 45 into the desired location of the venous vasculature of the liver selectively toward the target area. Subsequently in time the stable central venous pressure catheter 50 is threaded coaxially within the pull catheter 40 to its desired location distal to the tip of the pull catheter 40. Then, the push catheter 60 is threaded coaxially within the stable central venous pressure catheter 50 and is pushed forward via a selective route to a destination point within the target organ L. At the destination point, the catheters 40 and 60 are seated at their respective desired occluded positions in the vasculature. The sequential assembly of the flow control unit F is thus completed.

In the foregoing initial stage, the three catheters 40, 50 and 60 are put in position in a selected venous site with no flow through the control unit F. With the catheters in place and without initiating flow, the measurement of the central venous pressure by transducer 54 gives a real-time initial model of the system fluid dynamics of blood at the treatment site.

The system thus described can be said to have both fixed and variable properties. The fixed properties refer to the fixed position of each of the three catheters. The variable properties refer both to the background noise dynamics of the hepatic circulation, i.e. the hepatic artery, the portal vein, and the hepatic veins, and to the variable hydrodynamics of the fluid trajectories and wave motions induced by the actions of the push, pull and central catheters. The fixed and the variable aspects of the system are coupled together, and inextricably interrelated.

There is, however, no need to establish or define specific fluid flow equations of motion explicitly in order to verify that proper perfusion fluid flow paths and relations are established. The control or treatment unit functions as an analog fluid dynamic computing unit that during its use and operation implicitly computes the solution to the equations of motion for the network, and performs the perfusion treatment according to the desired flow paths and relationships. This is done without resorting to the explicit use of calculations, numbers, mathematical equations or physical equations of motion and such; the control unit during its use performs those kinds of computational tasks.

Two examples or models help to explain by analogy the kinds of differential equations of motion that are implicitly solved by operation of the control unit. One is a water-flow model that cascades; the other is a moving crowd model.

In the water-flow model, the size and shape of the catheters influence the motion of fluid through the catheters. Also, the motion of fluid in parallel and opposite directions, and orientation through the catheters and through the vascular beds obeys the physical laws related to pressure, flow rate, and volume. In the moving crowd model, the size and shape of the catheters influence the movement of particles through the catheters. Also, the movement of particles through the network conforms to the physical laws related to pressure, flow rate, and volume.

Once it has been established that the flow control unit F with the catheters 40, 50 and 60 is properly located in the area to be treated, a saline solution is introduced and circulated to set up the appropriate push-pull relation and flow parameters. Saline fluid is introduced and circulated while the contents of the pull syringe 70 are monitored. When the contents of the pull syringe indicate there is no leakage of blood, the establishment of the closed loop flow path through the treatment site is indicated as having been achieved.

An equilibrium of fluid pressures and flow forces is achieved between the fluid pressure in the in vivo closed loop flow path and those of the other vascular flow forces and pressures on the organ or body portion under investigation. In the liver, as disclosed above, the primary other vascular flow forces and pressures are, as previously noted, those from the hepatic artery and the portal vein.

Next, a radio-opaque dye is added into the saline solution already present in the closed loop flow path. The dye-containing solution is allowed to flow into the perfusion site so that a CAT image may be formed. With the infusion of the radio-opaque dye and the resultant image formed on the monitor M, a visible physically imparted characteristic pattern emerges in real time of the region within the organ between the distal ends of the push or infusion catheter 60 and the pull catheter 40. The image also is formed at the same time that the treatment administering catheters are in vivo at the site where retrograde perfusion of the organ is indicated. The image so formed provides a visible indication on the display monitor M of the established flow path.

Figure 8:
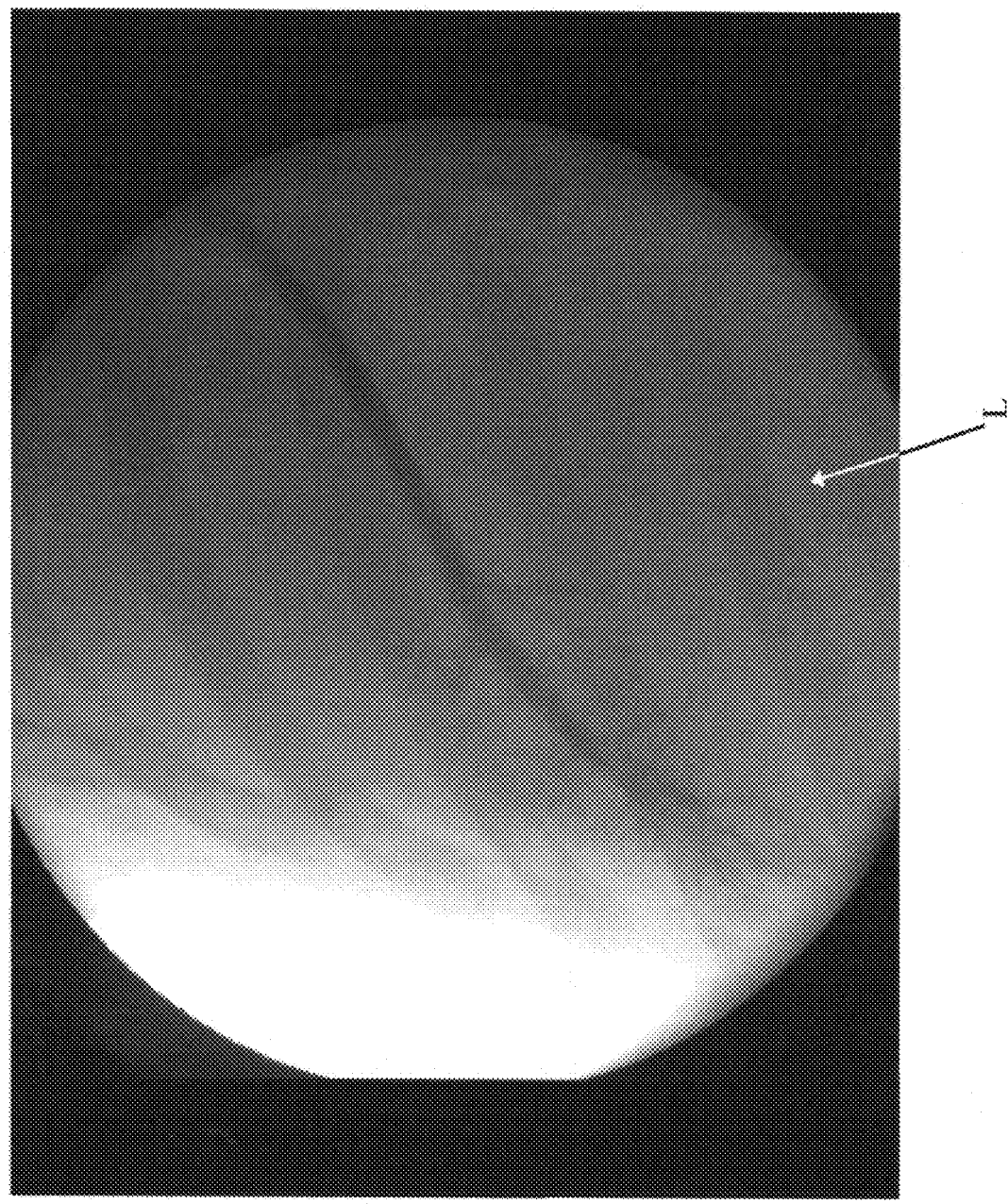
FIG. 8 is a display image of an animal liver during a perfusion treatment procedure according to the present invention.

FIG. 8 is, as noted above, a photographic image of such a flow path established in this manner. The image so formed can be considered as an in vivo volumetric fractal map of the fluid trajectories induced in the organ under treatment with the present invention. The map or image so formed serves as a visible record, much like a fractal map, of each of the three-dimensional volume, two-dimensional area, and perimeter of the controlled dynamic flow routes taken by infusates from the proximal end of the catheters to the outer boundary of the organ for an during retrograde perfusion. Several advantages result from such volumetric mapping. Current techniques of visualization provide no means to analyze self-similar fractal anatomical structures from the inside and extending to the outer boundary of the vascular venous tree. Nor do current techniques enable the correlation of the geometrical-visualizable properties of a physiological system with its dynamic physical properties. The image so formed also serves to allow the treating physician to formulate, predict and establish probable routes and trajectories to be taken thereafter by a desired therapeutic agent.

The present invention thus allows direct control and definition or establishment of the retrograde perfusion flow path for delivery of therapy by retrograde perfusion to an organ site in the body. The image so formed also serves to allow the treating physician to formulate, predict and establish probable routes and trajectories to be taken thereafter by a desired therapeutic agent. As can be seen, a definite and definable flow path, and in effect an in vivo flow map of the perfusion site, is formed and depicted. The treating physician is not presented with a vague and undefined image of the organ and flow path of the therapeutic agent.

Once the flow path is confirmed to be the desired one for access to the part of the organ to be treated, the chemotherapeutic agent is introduced at the established treatment site. The physician can with the in vivo loop so formed develop various strategies for the flow control unit F. The physician is given alternatives by using the flow control unit F as to how to organize differential pressures externally between the push syringe 76 moving fluid forward and the pull syringe 70 moving fluid outward through the in vivo loop formed at the tumor treatment site.

If desired, different chemotherapeutic agents, different dosages, different sequences and exposure times and various combinations of any one or more of these chemotherapeutic strategies may be implemented with the present invention while the flow control unit is at the treatment site. The pressure-monitoring central venous pressure catheter 50 is used to coordinate, monitor, and visualize transient changes in the central venous pressure at the in vivo treatment site during the operation of the flow control unit F. As noted, the closed loop in vivo flow path has been established and verified before the administration of the chemotherapeutic agent. The chemotherapeutic agent may, in addition to doxorubicin previously mentioned, be any of a number of treatment agents. Other treatment agents which are effective as anti-cancer treatment agents may, for example, include cyclophosphamides such as those known as Cytoxan®, and others; methotrexate; and prednisone. The present invention, with its closed loop flow path and mounting pressure within such a flow path is particularly adapted for administration of chemotherapeutic agents having possible side effects on other organs, even potentially severe side effects. An example, as mentioned above, is doxorubicin.

As shown in FIG. 8 on iodinated contrast material has been injected with the control unit F into a peripheral branch of a hepatic vein of an adult laboratory animal. FIG. 8 was obtained with the retrograde perfusion procedure described above in an equilibrium phase and with a net pressure of from about 8 to about 10 mm Hg. It is to be noted that opacification is obtained of the branches, with minimal parenchymal stain. Further, no opacification of the adjacent hepatic or portal veins is seen present.

Figure 7:
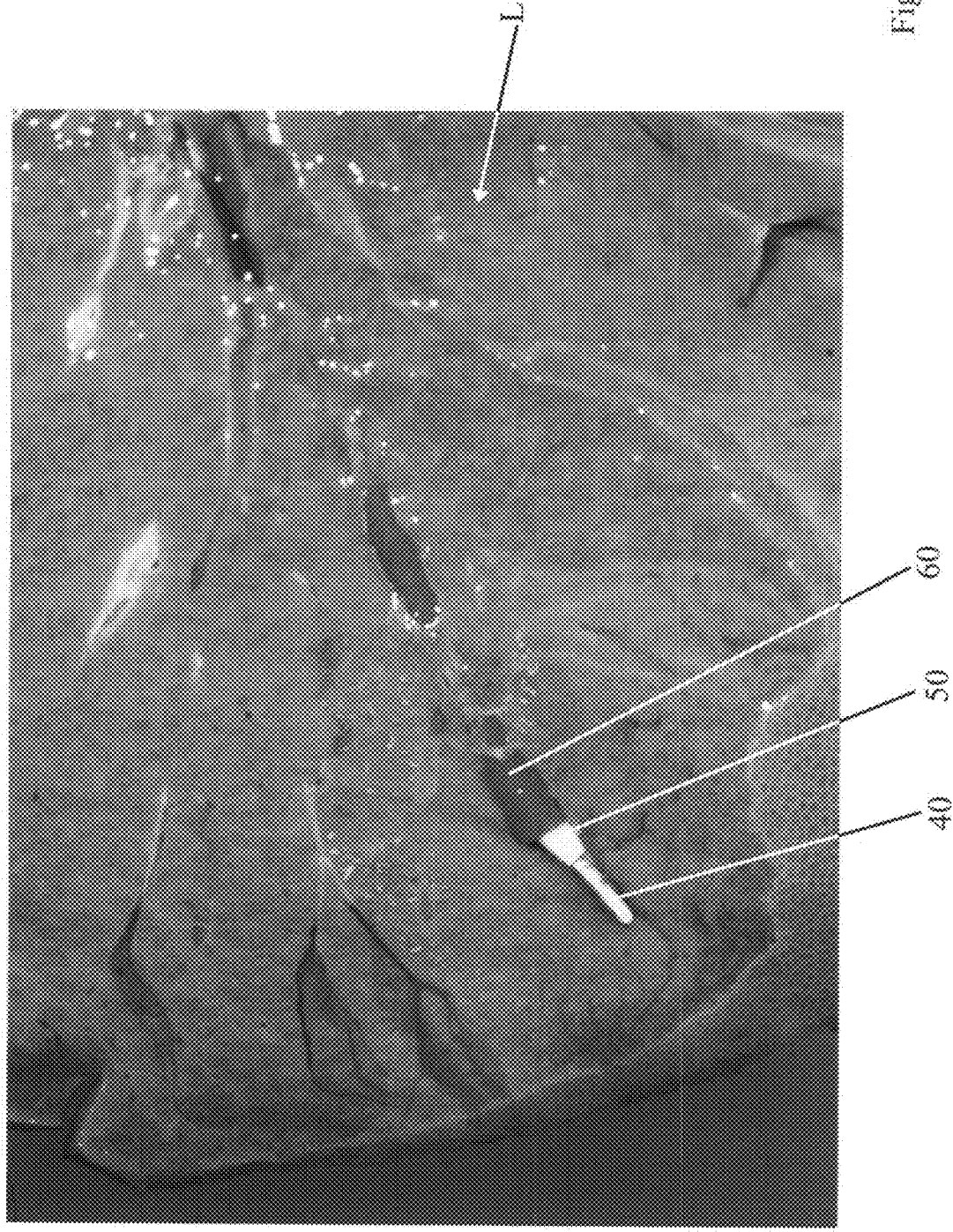
FIG. 7 is a photograph of an animal liver after a perfusion treatment procedure according to the present invention.

FIG. 7 is a photograph of a portion of the same liver from which the image of FIG. 8 was obtained. FIG. 7 depicts the results from a wedged hepatic venogram with an equilibrium phase after injection with a yellow color dye. In the equilibrium phase, infusion and withdrawal parameters were monitored so that no transsinusoidal leakage has occurred. The sample depicted in FIG. 7 confirms that no significant amount of any such leakage has occurred. No leakage of the fluids injected into the subject liver beyond the in vivo closed loop established with the present invention is perceptible in either of FIGS. 7 and 8. Because of this, compositions may be administered according to the present invention, which have not often used in the past, due to adverse side effects, such as those described above for doxorubicin, or due to system toxicity.

It should be noted and understood that there can be improvements and modifications made of the present invention described in detail above without departing from the spirit or scope of the invention as set forth in the accompanying claims.

What is claimed is:

1. A method of retrograde venous perfusion of a tumor in a patient's body, comprising the steps of:
    positioning a withdrawal catheter within vasculature of a target vessel in the patient's body near the tumor;
    positioning an infusion catheter within the vasculature of the target vessel extending beyond the withdrawal catheter and near the tumor;
    concentrically disposing a venous pressure catheter between the infusion catheter and the withdrawal catheter;
    occluding the vasculature in the target vessel with the infusion catheter and the withdrawal catheter to form a closed loop retrograde perfusion flow path through the target vessel between the positioned infusion catheter and the positioned withdrawal catheter;
    monitoring venous pressure at the venous pressure catheter in the closed loop flow path; and
    circulating a chemotherapeutic agent, the chemotherapeutic agent having side effects on other organs in the patient's body, from the infusion catheter through the closed loop flow path in the target vessel to the withdrawal catheter.

2. The method of claim 1, further including the steps of:
    circulating a saline fluid through the closed loop flow path in the target vessel prior to the step of circulating a chemotherapeutic agent; and
    establishing that the closed loop retrograde perfusion flow path is achieved with the saline fluid.

3. The method of claim 2, further including the step of:
    circulating a dye-containing solution through the closed loop retrograde perfusion flow path subsequent to the step of establishing that the closed loop retrograde flow path is achieved with the saline fluid.

4. The method of claim 3, further including the step of:
    forming a visible image of the established closed loop retrograde perfusion flow path.

5. A treatment unit for retrograde perfusion of a tumor in a patient's body, comprising:
    a withdrawal catheter for positioning within vasculature of a target vessel in the patient's body near the tumor;
    means with the withdrawal catheter for occluding the target vessel at a proximal end of the withdrawal catheter;
    an infusion catheter located within the withdrawal catheter for positioning within the vasculature of the target vessel vasculature of the patient's body near the tumor;
    means with the infusion catheter for occluding the target vessel at a proximal end of the infusion catheter to form a closed loop retrograde perfusion flow path through the target vessel between the occluding positioned infusion catheter and the occluding positioned withdrawal catheter;
    the infusion catheter circulating a chemotherapeutic agent from the infusion catheter through the closed loop flow path in the target vessel, the chemotherapeutic agent having side effects on other organs in the patient's body, for collection at the withdrawal catheter; and
    a venous pressure monitoring catheter for positioning within the vasculature of the target vessel concentrically disposed between the infusion catheter and the withdrawal catheter.

6. The treatment unit of claim 5, wherein the means for occluding the target vessel at a proximal end of the infusion catheter comprises a compliant catheter occlusion balloon.

7. The treatment unit of claim 5, wherein the means for occluding the target vessel at a proximal end of the infusion catheter comprises an outer wall of the infusion catheter.

8. The treatment unit of claim 5, wherein the means for occluding the target vessel at a proximal end of the withdrawal catheter comprises a compliant catheter occlusion balloon.

9. The treatment unit of claim 5, wherein the means for occluding the target vessel at a proximal end of the withdrawal catheter comprises an outer wall of the withdrawal catheter.

10. The treatment unit of claim 5, further including:
    a pressure transducer in communication with the venous pressure monitoring catheter.

11. The treatment unit of claim 10, wherein the pressure transducer is mounted within the venous pressure monitoring catheter.

12. The treatment unit of claim 10, wherein the pressure transducer is located externally of the patient's body.

13. A treatment unit for retrograde perfusion of a tumor in a patient's body, comprising:
    a withdrawal catheter for positioning within vasculature of a target vessel in the patient's body near the tumor;
    means disposed in communication with the withdrawal catheter for occluding the target vessel at a proximal end of the withdrawal catheter;
    an infusion catheter concentrically disposed within the withdrawal catheter for positioning within the vasculature of the target vessel vasculature of the patient's body near the tumor;
    means disposed in communication with the infusion catheter for occluding the target vessel at a proximal end of the infusion catheter to form a closed loop retrograde perfusion flow path through the target vessel between the occluding positioned infusion catheter and the occluding positioned withdrawal catheter;
    the infusion catheter circulating a chemotherapeutic agent from the infusion catheter through the closed loop flow path in the target vessel, the chemotherapeutic agent having side effects on other organs in the patient's body, for collection at the withdrawal catheter; and
    a venous pressure monitoring catheter for positioning within the vasculature of the target vessel concentrically disposed within the withdrawal catheter.

* * * * *